United States Patent [19]

Morita et al.

[11] Patent Number: 4,574,156
[45] Date of Patent: Mar. 4, 1986

[54] POLYMETHOXYBENZYL PIPERAZINE DERIVATIVES EFFECTIVE FOR IMPROVING BLOOD CIRCULATION SYSTEM

[75] Inventors: Masao Morita, Hirakata; Jiro Sugimoto, Yao; Komei Mizuno, Takatsuki; Motoaki Tanaka, Urawa; Fumiyoshi Urano, Niiza, all of Japan

[73] Assignee: Wako Pure Chemical Industries, Ltd., Osaka, Japan

[21] Appl. No.: 679,346

[22] Filed: Dec. 7, 1984

[30] Foreign Application Priority Data

Dec. 10, 1983 [JP] Japan .................. 58-233404

[51] Int. Cl.⁴ ............... C07D 295/00; A61K 31/495
[52] U.S. Cl. .................... 544/398; 544/401
[58] Field of Search ............... 544/398, 401; 514/255

[56] References Cited

U.S. PATENT DOCUMENTS 4,100,285  7/1978  Murai et al. .................. 424/250

FOREIGN PATENT DOCUMENTS 6154474  11/1981  Japan .................. 544/398
7131776  8/1982  Japan .................. 544/398

Primary Examiner—Donald G. Daus
Assistant Examiner—Cecilia Shen
Attorney, Agent, or Firm—Armstrong, Nikaido, Marmelstein & Kubovcik

[57] ABSTRACT

A compound of the formula:

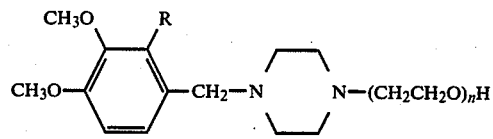

($R=H$, $CH_3O$; $n=2$ to 5) is effective for improving blood circulation system.

6 Claims, 2 Drawing Figures

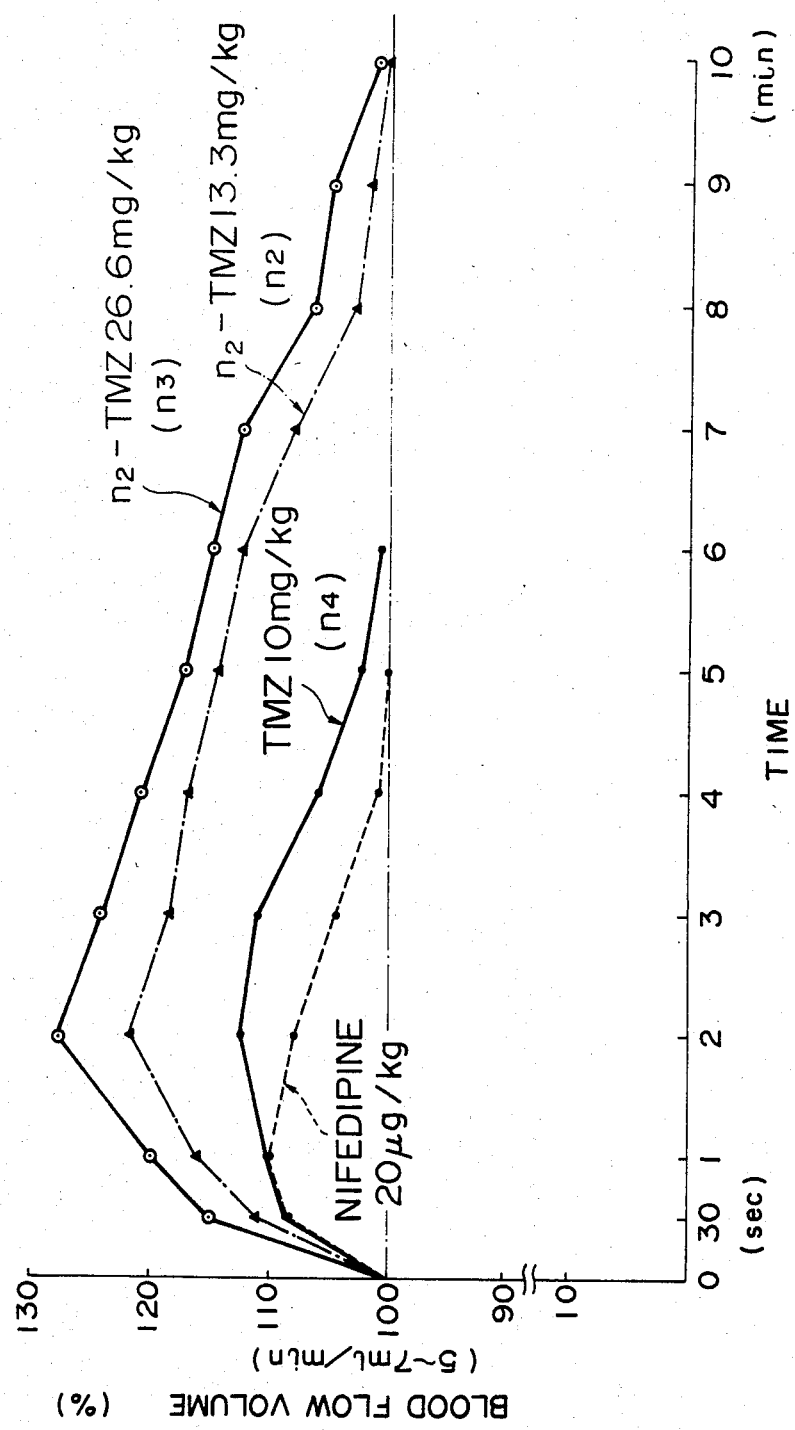

POLYMETHOXYBENZYL PIPERAZINE DERIVATIVES EFFECTIVE FOR IMPROVING BLOOD CIRCULATION SYSTEM

BACKGROUND OF THE INVENTION

This invention relates to polymethoxybenzyl piperazine derivatives, processes for producing the same and blood circulation system improving agents using the same.

In recent years, great hopes have been placed on curative or preventive drugs for diseases in circulatory systems such as cerebral circulation system, coronary circulation system and the like, and in order to meet the demand, various drugs have been made fit for practical use. However, such drugs often require administration for a long period of time, and there is desired a drug which is safe and has excellent effect at a smaller dose.

The present inventors has noted that trimetazidine, a coronary vasodilator, has an effect of stabilizing myocardium, almost completely prevents actions of factors causing angina pectoris on myocardium, and hence contributes to stabilization of myocardial actions. In addition, the present inventors have judged that the duration in blood of trimetazidine administered is not so long, so that no desired drug efficacy is obtained. In order to obtain the desired drug by improving the defects of trimetazidine without losing its properties, the present inventors have devoted themselves to study while investigating the correlation between chemical structure and drug efficacy and have consequently accomplished this invention.

On the other hand, U.S. Patent No. 4,100,285 discloses N-substituted trialkoxybenzyl piperazine derivatives, but they are rather high in toxicity, and too large in lowering in the heart rate and hence not satisfactory.

SUMMARY OF THE INVENTION

An object of this invention is to provide polymethoxybenzyl piperazine derivatives usable as blood circulation improving agents which are low in toxicity, are excellent in drug efficacy, can be used for curing a fit of angina pectoris, and can continuously be administered for preventing the fit.

This invention provides a compound represented by the formula:

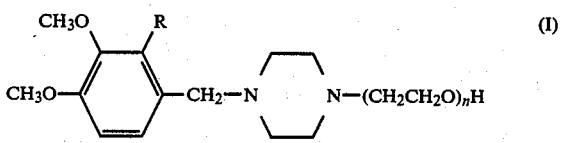

wherein R is hydrogen or a methoxy group and n is an integer of 2 to 5, or a pharmaceutically acceptable acid adduct thereof, processes for producing the same and a pharmaceutical composition using the same as active ingredient.

BRIEF DESCRIPTION OF THE DRAWINGS

FIG. 2 is a graph showing an influence on blood flow volume in rat abdominal aorta.

DESCRIPTION OF THE PREFERRED EMBODIMENTS

Figure 1:
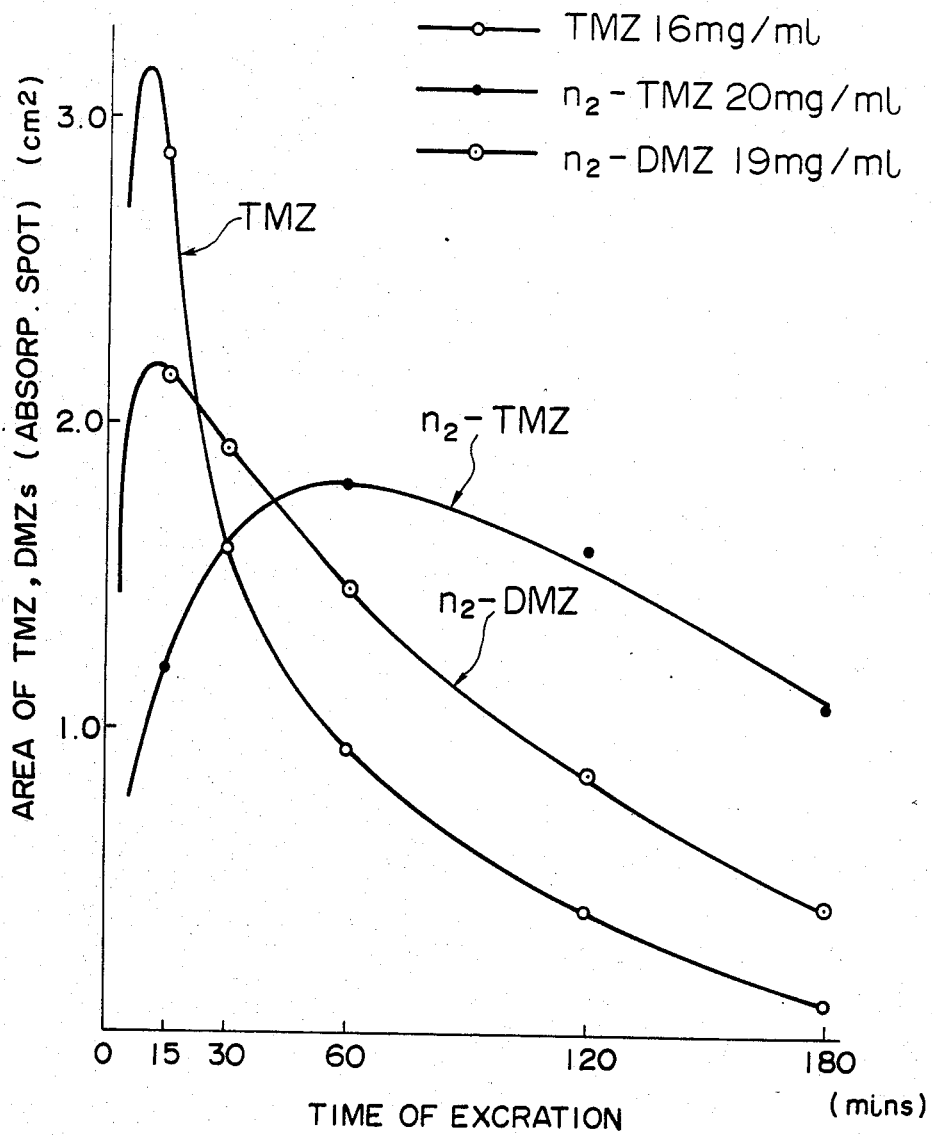
FIG. 1 is a graph showing excretion curves.

All the compounds of di- or trimethoxybenzyl-piperazino ether-linkage-containing alkanols of this invention are novel compounds not described in literature. They have a pharmacological action on blood circulation system such as coronary circulation system, e.g. depression of abnormal excitation of cardiac movement, depression of constriction of coronary artery, depression of resistance of peripheral circulatory, and the like. Further, an increase in blood flow volume can be attained with such a small dosage as not to lower the maximum blood pressure as a result of the depression of resistance of peripheral circulatory. Thus these compounds are safe and useful as drugs, for example, curative and preventive drugs against ischemic heart diseases, drugs against increased resistance of peripheral circulatory, etc.

A method for most accurately evaluating and judging the drug efficacy of the compounds of this invention has already been disclosed in Japanese Circulation Journal Vol. 34, No. 8, p. 725-732 (1970) by some of the present inventors. The method shown therein comprises determining to what extent the termination of rhythm of removed guinea pig atrium by addition of G-strophanthin (ovabaïne) can be delayed by a previously or simultaneously given drug, and thereby judging the drug efficacy. According to said method, the following results were obtained.

Rhythm of a removed guinea pig atrium sample in an oxygen-saturated Ringer's solution at 30° C. was stopped in 36.2±11.7 minutes by addition of G-strophanthin to the Ringer's solution in an amount of $1.5 \times 10^{-6}$ g/ml ($2.6 \times 10^{-3}$ m Mol). When for example, $3 \times 10^{-4}$ Mol of trimetazidine or the compound of this invention were added to the medium before or simultaneously with the addition of G-strophanthin, the duration of rhythm was greatly prolonged in both cases. However, while trimetazidine caused a prolongation up to 180 minutes, the compound of this invention was more effective than trimetazidine. These data were confirmed by experimental measurement repeated 8 times for each case. One reason of the prolongation seems to be as follows. The decrease of potassium ions in cardiac muscle caused by G-strophanthin is prevented by the effects of protecting and stabilizing myocardium of the drugs described above.

Another reason for usefulness of the compounds of this invention is that they are very low in toxicity. While LD$_{50}$ for intraperitoneal injection to mouse of trimetazidine is 300 to 310 mg/kg, that of all the compounds of this invention is 1,000 to 1,250 mg/kg.

The compounds of this invention can be produced by a few efficient and useful processes. Although processes other than the following processes can be employed, the following processes are more preferable in consideration of industrial production. The processes of this invention are formulated as follows. In the formulae, R and n are as defined above; X is halogen; l and m are integers, l is 0 to 4 and l+m=n, and m+l is preferably 2 to 5.

Process A

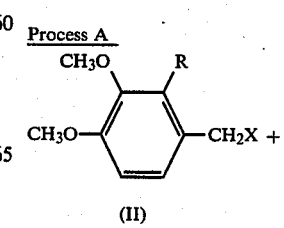

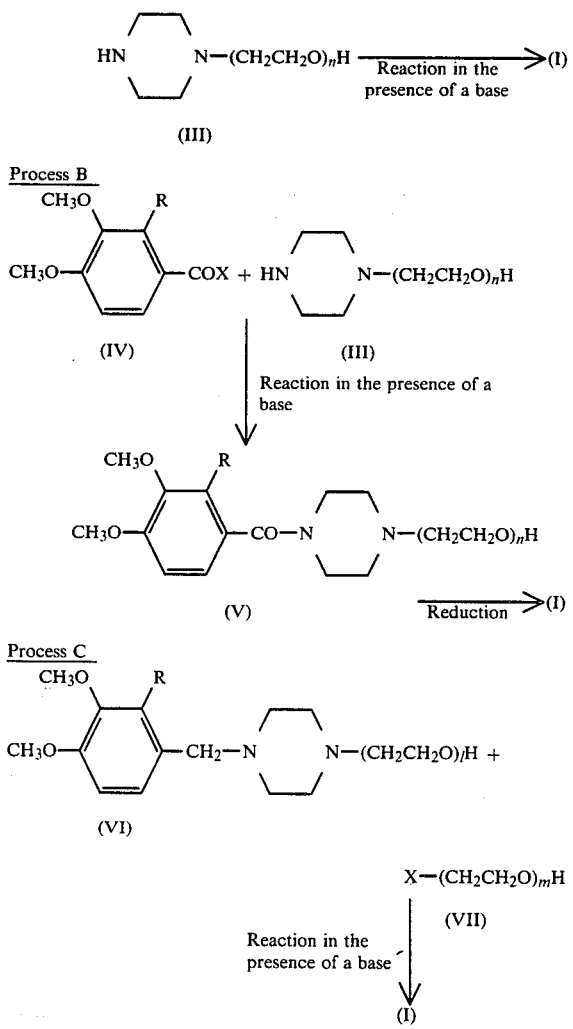

Outlines of typical procedures for the individual processes are as follows.

Process A: A di-or trimethoxybenzyl halide of the formula (II) is reacted with a piperazine derivative of the formula (III) having a terminal OH group with heating in an organic solvent in the presence of a base, and hydrochloride of the desired compound of the formula (I) is deposited from the organic layer after washing with water, for example, by addition of hydrogen chloride, and then is isolated.

The halogen constituting said halide is usually chlorine or bromine. As the base used in the reaction, inorganic compounds such as sodium carbonate, potassium carbonate, sodium hydrogencarbonate, potassium hydrogen-carbonate, sodium hydroxide, potassium hydroxide and the like and organic bases such as triethylamine, pyridine, piperidine, piperazine and the like are effective. As the organic solvent, there can be used, without any particular limitation, those which do not react with the starting materials and the product except for acids, for example, hydrocarbons such as benzene, toluene, xylene, cyclohexane and the like, halogenated hydrocarbons such as chloroform, dichloroethane, carbon tetrachloride and the like, ethyl acetate, tetrahydrofuran, ethyl ether, isopropyl ether, methyl Cellosolve, ethyl Cellosolve, dioxane, dimethylformamide, acetonitrile, etc. It is usually sufficient that the reaction is carried out for several hours at the reflux temperature of the organic solvent used. When the reaction temperature is lower than the reflux temperature, the reaction time increases.

Process B: A di-or trimethoxybenzoyl halide of the formula (IV) is mixed with a piperazine derivative of the formula (III) having a terminal OH group in the presence of an organic solvent and reacted therewith with heating, after which the reaction product is reduced with an appropriate reducing agent and then isolated as in Process A.

The same halogen constituting said acid halide and the same base and the same solvent as used in Process A can be used. In order to allow the reaction proceed mildly, the starting material of the formula (III) and the base are usually mixed and then placed in the solvent, and a solution of the starting material of the formula (IV) in the organic solvent is added thereto with stirring and with cooling to about 15° C. or lower, after which the resulting mixture is heated to room temperature or a little higher. In some cases, it is heated to the reflux temperature of the solvent finally, whereby the reaction in the first step is completed.

As a method for the reduction in the second step, any method for reducing an acid halide of this kind may be used. For example, reduction with diborane in tetrahydrofuran, reduction with lithium aluminum hydride in ether, reduction with sodium dihydrobis(2-methoxyethoxy)aluminate using benzene, toluene or the like as a solvent, etc. are effective.

Process C: A di-or trimethoxybenzyl piperazine of the formula (VI) (in the case of l being 0) or an ether linkage-containing alkanol substituted thereby (in the case of l being 1 to 4) is reacted with a mono-, di-, tri- or tetraethylene glycol monohalohydrin of the formula (VII) with heating in an organic solvent in the presence of a base, and after the solvent is removed by distillation, the residue is subjected to column separation, whereby the desired compound of the formula (I) is isolated.

As the base, in the case of l being 0, sodium hydride, metallic sodium, triethylamine, diethylamine and the like are suitable, and in the case of l being 1 to 4, sodium hydride, metallic sodium and the like are suitable. As the halogen in the formula (VII), chlorine or bromine is suitable. As the solvent, hydrocarbons such as n-hexane, n-octane, benzene, cyclohexane, toluene, xylene and the like and ethers such as ethyl ether, isopropyl ether, tetrahydrofuran and the like are suitable.

Needless to say, when one of the compounds of this invention is produced by any of Process A, Process B and Process C, these processes yield the same product having the same physical properties. The production processes of this invention are applicable to all the compounds of this invention.

After being obtained by the above-mentioned Process A, Process B or Process C, the compound of this invention can conveniently be isolated and purified as a salt with an inorganic acid such as hydrochloric acid, sulfuric acid, nitric acid or the like or an organic acid such as oxalic acid, acetic acid, tartaric acid, fumaric acid, benzenesulfonic acid or the like. In view of the intention of administering said compound as a drug, it is desirable to make said compound into a salt with hydrochloric acid, tartaric acid, citric acid, lactic acid, malic acid or the like. Further, the compounds of this invention are very stable in an aqueous solution and cause no anxiety for preparation and storage even when made into an injection. This is because they have no portion to be deteriorated in their chemical structures. Said compounds are advantageous in that they can sufficiently be formed into a desired pharmaceutical form.

This invention is illustrated by way of the following Examples.

EXAMPLE 1

N-2-(2-Hydroxyethoxy)ethyl-N'-2,3,4-trimethoxybenzyl piperazine dihydrochloride (Compound of the formula (I) in which R is a methoxy group and n is 2).

A mixture of 2,3,4-trimethoxybenzyl chloride (21.7 g.), 2-(2-hydroxyethoxy)ethylpiperazine(17.4 g.) and anhydrous sodium carbonate(10.6 g.) was refluxed with vigorous stirring in benzene(200 ml.) for 3 hours. The mixture was cooled to room temperature, washed with water (100 ml.), dried, and evaporated to a syrup. The residue was dissolved in ether, saturated with dry hydrogen chloride, and the solid which deposited was collected by filtration. Recrystallization of this solid from methanol gave the title compound(36.3 g.) as colorless needles, mp. 214° C. (decomp.).

Analysis calcd. for $C_{18}H_{30}N_2O_5 \cdot 2HCl$: C, 50.59; H, 7.55; N, 6.55. Found: C, 50.41; H, 7.50; N, 6.88.

$^1$HNMR($D_2O$)δ(ppm): 3.55~3.82(16H, m, piperazinium protons, $CH_2CH_2O\times2$), 3.92, 3.94, 4.01 (each 3H, each S, $CH_3O\times3$), 4.52(2H, S, $A_rCH_2N<$), 6.95, 7.31(each 1H, each d, J=9 Hz, aromatic protons)

IR$\nu_{max}^{KBr}$(cm$^{-1}$): 3400(OH), 2900, 2450-2650

1605(C=C).

When the alcoholic solution saturated with oxalic acid or tartaric acid was added to the ethereal solution of the above-mentioned syrupy residue with cooling, there was obtained oxalate(mp. 222° C.) or tartarate (mp. 246° C.), respectively.

EXAMPLE 2

N-2-[2-(2-Hydroxyethoxy)ethoxy]ethyl-N'-3,4-dimethoxybenzyl piperazine dihydrochloride (Compound of the formula(I) in which R is hydrogen and n is 3).

A mixture of 3,4-dimethoxybenzyl bromide(23.1 g.), 2-[2-(2-hydroxyethoxy)ethoxy]-ethyl piperazine(21.8 g.) and triethylamine(10.1 g.) was refluxed with stirring in toluene for 3 hours. The reaction mixture was cooled to room temperature, washed with water, dried, and evaporated. The syrupy residue was dissolved in ethanol, then saturated with dry hydrogen chloride. The solid which deposited was collected by filtration, and recrystallized from ethanol to give the title compound(37.5 g.) as colorless needles, mp. 195° C. (decomp.).

Analysis calcd. for $C_{19}H_{32}N_2O_5 \cdot 2HCl$: C, 51.70; H, 7.76; N, 6.35. Found: C, 51.55; H, 7.95; N, 6.24.

$^1$HNMR($D_2O$)δ(ppm): 3.47~3.80(20H, m, piperazinium protons, $CH_2CH_2O\times3$), 3.92(6H, S, $CH_3O\times2$), 4.50(2H, S, $A_rCH_2N<$), 7.16(3H, S, aromatic protons).

IR$\nu_{max}^{KBr}$(cm$^{-1}$): 3400(OH), 2900, 2350-2600

1610, 1595(C=C).

When tartaric acid or citric acid saturated in ethanol was added to the alcoholic solution of the aforesaid syrupy residue with cooling, there was obtained tartarate (mp. 236° C.) or citrate (mp. 218° C.).

EXAMPLE 3

N-2-[2-(2-Hydroxyethoxy)ethoxy]ethyl-N'-2,3,4-trimethoxybenzyl piperazine dihydrochloride (Compound of the formula(I) in which R is a methoxy group and n is 3).

A mixture of 2,3,4-trimethoxybenzyl chloride (21.7 g.), 2-[2-(2-hydroxyethoxy)ethoxy]-ethyl piperazine (21.8 g.) and anhydrous sodium carbonate(10.6 g.) was refluxed with stirring in benzene for 3 hours. Thereafter, the same procedure as in Example 1 was followed, and recrystallization from ethanol was carried out to give the title compound (35.4 g.) as colorless needles, mp. 186° C. (decomp.).

Analysis calcd. for $C_{20}H_{34}N_2 \cdot 2HCl$: C, 50.96; H, 7.70; N, 5.94. Found: C, 51.06; H, 7.76; N, 6.05.

$^1$HNMR($D_2O$)δ(ppm): 3.60 ~3.80(20H, m, piperazinium protons, $CH_2CH_2O\times3$), 3.92, 3.95, 4.01(each 3H, each S, $CH_3O\times3$), 4.52(2H, S, $A_rCH_2N<$) 6.96, 7.31(each 1H, each d, J=9 Hz, aromatic protons).

IR$\nu_{max}^{KBr}$(cm$^{-1}$): 3400(OH), 2900, 2350-2550

1605(C=C).

EXAMPLE 4

N-2-[2-{2-(2-Hydroxyethoxy)ethoxy}ethoxy]ethyl-N'-3,4-dimethoxybenzyl piperazine dihydrochloride (Compound of the formula(I) in which R is hydrogen and n is 4).

Anhydrous potassium carbonate(13.8 g.) was added to a solution of 3,4-dimethoxybenzyl chloride (18.7 g.) and 2-[2-{2-(2-hydroxyethoxy)ethoxy}ethoxy]ethyl piperazine (26.2 g.) in 1,2-dichloroethane, the mixture was refluxed with vigorous stirring for 5 hours. Thereafter, the same procedure as described in Example 1 was followed and recrystallization from ethanol gave the title compound (31.5 g.) as colorless microneedles, mp. 155° C. (decomp.).

Analysis calcd. for $C_{21}H_{36}N_2O_6 \cdot 2HCl$: C, 51.96; H, 7.89; N, 5.77. Found: C, 51.88; H, 7.93; N, 5.80.

$^1$HNMR($D_2O$)δ(ppm): 3.57~3.77(24H, m, piperazinium protons, $CH_2CH_2O\times4$), 3.91(6H, S, $CH_3O\times2$), 4.50(2H, S, $A_rCH_2N<$), 7.14(3H, S, aromatic protons)

IR$\nu_{max}^{KBr}$(cm$^{-1}$): 3400(OH), 2900, 2350-2600

1605, 1595(C=C).

EXAMPLE 5

N-2-[2-[2-{2-(2-Hydroxyethoxy)ethoxy}ethoxy]ethyl-N'-3,4-dimethoxybenzyl piperazine dihydrochloride (Compound of the formula(I) in which R is hydrogen and n is 5).

A mixture of 3,4-dimethoxybenzyl chloride (18.7 g.), 2-[2-[2-{2-(2-hydroxyethoxy)ethoxy}ethoxy]ethoxy]ethyl piperazine (30.6 g.) and anhydrous potassium carbonate (13.8 g.) was refluxed with stirring in 1,2-dichloroethane for 5 hours. Thereafter, the same procedure as described in Example 4 was followed and recrystallization from ethanol gave the title compound (31.7 g.) as colorless microneedles, mp. 155° C. (decomp.).

Analysis calcd. for $C_{23}H_{40}N_2O_7.2HCl$: C, 52.17; H, 8.00; N, 5.29. Found: C, 52.03; H, 8.01; N, 5.40.

$^1HNMR(D_2O)\delta$(ppm): 3.56~3.73(28H, m, piperazinium protons, $CH_2CH_2O \times 5$), 3.90(6H, S, $CH_3O \times 2$), 4.45(2H, S, $A_rCH_2N<$), 7.13(3H, S, aromatic protons).

$IR\nu_{max}^{KBr}(cm^{-1})$: 3400(OH), 2900, 2350-2600

1610, 1595(C=C).

EXAMPLE 6

N-2-[2-[2-{2-(2-Hydroxyethoxy)ethoxy}ethoxy]ethoxy]ethyl-N'-2,3,4-trimethoxybenzyl piperazine dihydrochloride (Compound of the formula(I) in which R is a methoxy group and n is 5).

A mixture of 2,3,4-trimethoxybenzyl chloride (21.7 g.), 2-[2-[2-{2-(2-hydroxyethoxy)ethoxy}ethoxy]ethoxy]ethyl piperazine(30.6 g.) and anhydrous potassium carbonate (13.8 g.) was refluxed with vigorous stirring in toluene for 5 hours. Thereafter, the same procedure as in Example 4 was followed and recrystallization from ethanol was carried out to obtain the title compound (33.6 g.) as colorless microneedles, mp. 119° C. (decomp.).

Analysis calcd. for $C_{24}H_{42}N_2O_8.2HCl$: C, 51.52; H, 7.93; N, 5.01. Found: C, 51.44; H, 7.90; N, 5.25.

$^1HNMR(D_2O)\delta$(ppm): 3.50~3.70(28H, m, piperazinium protons, $CH_2CH_2O \times 5$), 3.87, 3.90, 3.96(each 3H, each S, $CH_3O \times 3$), 4.45(2H, S, $A_rCH_2N<$), 6.92, 7.23(each 1H, each d, J=9 Hz, aromatic protons).

$IR\nu_{max}^{KBr}(cm^{-1})$: 3400(OH), 2900, 2440-2650

1610(C=C).

EXAMPLE 7

N-2-[2-{2-(2-Hydroxyethoxy)ethoxy}ethoxy]ethyl-N'-2,3,4-trimethoxybenzyl piperazine dihydrochloride (Compound of the formula(I) in which R is a methoxy group and n is 4).

A mixture of 2,3,4-trimethoxybenzyl chloride (21.7 g.), 2-[2-{2-(2-hydroxyethoxy)ethoxy}ethoxy]ethyl piperazine(26.2 g.) and anhydrous sodium carbonate(10.6 g.) was stirred in 1,4-dioxane at 80°-90° C. for 5 hours. Thereafter, the same procedure as in Example 2 was followed and recrystallization from ethanol gave the title compound (34.0 g.) as colorless microneedles, mp. 139° C. (decomp.).

Analysis calcd. for $C_{22}H_{38}N_2O_7.2HCl$: C, 51.26; H, 7.82; N, 5.43. Found: C, 50.98; H, 7.95; N, 5.55.

$^1HNMR(D_2O)\delta$(ppm): 3.56~3.75(24H, m, piperazinium protons, $CH_2CH_2O \times 4$), 3.89, 3.92, 3.98(each 3H, each S, $CH_3O \times 3$), 4.48(2H, S, $A_rCH_2N<$), 6.93, 7.27(each 1H, each d, J=9 Hz, aromatic protons).

$IR\nu_{max}^{KBr}(cm^{-1})$: 3400(OH), 2900, 2450-2650

1610(C=C).

EXAMPLE 8

N-2-(2-Hydroxyethoxy)ethyl-N'-3,4-dimethoxybenzyl piperazie dihydrochloride (Compound of the formula(I) in which R is hydrogen and n is 2).

A mixture of 3,4-dimethoxybenzyl chloride (18.7 g.), 2-(2-hydroxyethoxy)ethyl piperazine(17.4 g.) and anhydrous sodium carbonate(10.6 g.) was refluxed with stirring in toluene for 3 hours. Thereafter, the same procedure as in Example 1 was followed and recrystallization from methanol gave the title compound(33.8 g.) as colorless leaflets, mp. 205° C. (decomp.).

Analysis calcd. for $C_{17}H_{28}N_2O_4.2HCl$: C, 51.39; H, 7.61; N, 7.05. Found: C, 51.48; H, 7.58; N, 6.91.

$^1HNMR(D_2O)\delta$(ppm): 3.60~3.83(16H, m, piperazinium protons, $CH_2CH_2O \times 2$), 3.93(6H, S, $CH_3O \times 2$), 4.51(2H, S, $A_rCH_2N<$), 7.15(3H, S, aromatic protons).

$IV\nu_{max}^{KBr}(cm^{-1})$: 3350(OH), 2900, 2400-2650

1610, 1595(C=C).

EXAMPLE 9

N-2-(2-Hydroxyethoxy)ethyl-N'-3,4-dimethoxybenzyl piperazine dihydrochloride (Compound of the formula(I) in which R is hydrogen and n is 2).

A solution of 3,4-dimethoxybenzyl chloride (20.1 g.) in benzene was added dropwise to a stirred solution of 2-(2-hydroxyethoxy)ethyl piperazine(17.4 g.) and triethylamine(10.1 g.) in benzene at 0°-15° C. and the mixture was stirred at room temperature for 3 hours. The precipitated solid was filtered off and the filtrate was evaporated in vacuo to a dark viscous oil residue. The residue was dissolved in tetrahydrofuran and was added dropwise to a stirred solution(200 ml.) of tetrahydrofuran containing diborane in a concentration of 1 M. at 0°±3° C., after which the mixture was refluxed with stirring for one hour. The mixture was acidified with dil. hydrochloric acid at room temperature and then concentrated. The residue of the aqueous layer was basified with sodium hydroxide, extracted with ether, dried and saturated with dry hydrogen chloride. The precipitate was collected by filtration and recrystallized from methanol to give the title compound (27.0 g.) as colorless leaflets, mp. 205° C. (decomp.). Its spectra were identical with those of the product described in Example 8.

Example 10

N-2-[2-(2-Hydroxyethoxy)ethoxy]ethyl-N'-2,3,4-trimethoxybenzyl piperazine dihydrochloride (Compound of the formula(I) in which R is a methoxy group and n is 3).

A solution of 2,3,4-trimethoxybenzyl chloride (2.3 g.) in ether was added dropwise to a stirred solution of 2-[2-(2-hydroxyethoxy)ethoxy]ethyl piperazine(2.2 g.) and anhydrous sodium carbonate(1.1 g.) in ether at 0°–15° C., and the mixture was refluxed with stirring for one hour. The mixture was cooled to room temperature, the precipitate was filtered off, and the filtrate was added dropwise to a suspension of lithium aluminum hydride (0.5 g.) in ether at room temperature. Then, the mixture was refluxed with stirring for 2 hours. The resulting mixture was cooled to room temperature, poured into water and basified with aqueous sodium hydroxide. The organic phase was separated, washed with water, dried, and saturated with dry hydrogen chloride. The precipitate was collected by filtration and recrystallized from ethanol to provide the title compound(3.3 g.) as colorless needles, mp. 186° C. (decomp.). Its spectra were identical with those of the product described in Example 3.

Example 11

N-2-(2-Hydroxyethoxy)ethyl-N'-2,3,4-trimethoxybenzyl piperazine dihydrochloride (Compound of the formula(I) in which R is a methoxy group and n is 2).

A mixture of N-2,3,4-trimethoxybenzyl piperazine (2.7 g.), diethylene glycol monochlorohydrin (1.3 g.) and triethylamine(1.0 g.) in xylene was refluxed with stirring for 25 hours, poured into water (10 ml.). The organic phase was separated, washed with water, dried, and concentrated under reduced pressure. The dark oil residue was chromatographed over a column 80 cm in height and 1.5 cm in diameter containing 30 g. of silica gel (Wako Gel C-200) using 3/1 benzene-methanol solvent mixture. There was obtained 2.0 g. of product(pale yellowish viscous oil). TLC showed one major component (Rf value 0.20).

Analysis calcd. for $C_{18}H_{30}N_2O_5$: C, 60.99; H, 8.53; N, 7.90. Found : C, 61.07; H, 8.68; N, 8.04.

MS(m/e): 354 (M+).

This viscous oil was dissolved in ether, saturated with dry hydrogen chloride, and the solid which deposited was collected. Recrystallization from methanol gave the title compound as colorless needles, mp. 214° C. (decomp.), whose spectra were identical with those of the product described in Example 1.

Example 12

N-2-[2-(2-Hydroxyethoxy)ethoxy]ethyl-N'-3,4-dimethoxybenzyl piperazine dihydrochloride (Compound of the formula(I) in which R is hydrogen and n is 3).

A solution of N-2-(2-hydroxyethoxy)ethyl-N'-3,4-dimethoxybenzyl piperazine(6.5 g.) in benzene was added dropwise to a suspension of sodium hydride (0.7 g.) in benzene, and the mixture was refluxed with stirring for one hour, cooled to room temperature. To the resulting mixture was added ethylene chlorohydrin(1.6 g.) at room temperature, was stirred under reflux for 4 hours and the same procedure as described in Example 11 was followed. There was obtained 5.0 g. of product (pale yellowish viscous oil). TLC showed one major component(Rf value 0.33).

Analysis calcd. for $C_{19}H_{32}N_2O_5$: C, 61.93; H, 8.75; N, 7.60. Found: C, 61.97; H, 9.00; N, 7.71.

MS(m/e): 368 (M+).

The viscous oil was dissolved in ethanol, saturated with dry hydrogen chloride, and the precipitate was collected by filtration. Recrystallization from ethanol afforded the title compound as colorless needles, mp. 195° C. (decomp.), whose spectra were identical with those of the product described in Example 2.

Example 13

N-2-[2-[2-{2-(2-Hydroxyethoxy)ethoxy}ethoxy]ethoxy]ethyl-N'-2,3,4-trimethoxybenzyl piperazine dihydrochloride (Compound of the formula (I) in which R is a methoxy group and n is 5).

A solution of N-2-(2-hydroxyethoxy)ethyl-N'-2,3,4-trimethoxybenzyl piperazine (7.1 g.) in benzene was added dropwise to a suspension of sodium hydride (0.7 g.) in benzene, and the mixture was refluxed with stirring for one hour. Triethylene glycol monochlorohydrin (3.4 g.) was added to the resulting mixture at room temperature, was stirred under reflux for 4 hours and the mixture was poured into water. The organic phase was separated, washed with water, dried, and evaporated under reduced pressure. The oil residue was chromatographed over a column 80 cm in height and 1.5 cm in diameter containing 30 g. of Wako Gel C-200 using 3/1 benzene-methanol solvent mixture. There was obtained 5.3 g. of product (pale yellowish viscous oil). TLC showed one major component (Rf value 0.35).

Analysis calcd. for $C_{21}H_{42}N_2O_8$: C, 59.24; H, 8.70; N, 5.76. Found: C, 59.44; H, 8.81, N, 5.90.

MS(m/e): 487 (M+)

The viscous oil was dissolved in ethanol, saturated with dry hydrogen chloride and the precipitate was collected by filtration. Recrystallization of this precipitate from ethanol gave the title compound as colorless microneedles, mp. 119° C. (decomp.), whose spectra were identical with those of the product described in Example 6.

Example 14

The fundamental pharmacological experiments described below were carried out by using the compounds of this invention and commercially available trimetazidine.

(1) $LD_{50}$ for intraperitoneal injection to mouse

| | |
|---|---|
| Trimetazidine | 300–310 mg/kg |
| Compounds of this | 1000–1250 mg/kg |

-continued
invention (2) Excretion curve

An intraperitoneal injection was given to three mice weighing 30 g, 35 g and 40 g, and the amount of each injection excreted with the lapse of time was measured by a thin layer chromatography (Cellulose f sheet of Merck & Co., Inc., upper layer of solvent system: n-BuOH: AcOH:$H_2O$=4:1:5 by volume) and UV absorption (2537 Å). The concentrations of the injections were 16 mg/ml for TMZ (trimetazidine), 20 mg/ml for $n_2$-TMZ (a compound of the formula(I) in which R=a methoxy group and n=2) and 19 mg/ml for $n_2$-DMZ (a compound of the formula(I) in which R=H and n=2).

The results were as shown in FIG. 1. As is clear from FIG. 1, trimetazidine is almost excreted at a time and hence is not desirable. On the other hand, $n_2$-TMZ is excreted slowly over a long period of time and hence is very desirable. $n_2$-DMZ is excreted a little more quickly than $n_2$-TMZ but is far superior to trimetazidine.

(3) Influence on blood flow volume in rat abdominal aorta

Male S.D. rats weighing 300±10 g were subjected to laparotomy under urethane anethesia, and the blood flow volume of abdominal aorta was measured by means of an electromagnetic rheometer simultaneously with the blood pressure in carotid artery. Each solution of drugs was administrated intravenously in an amount of 0.20-0.22 ml.

The results were as shown in FIG. 2. Since TMZ had almost no influence at a dose of 5 mg/kg, its influence at a dose of 10 mg/kg (n 4) was plotted in FIG. 2.

As is clear from FIG. 2, $n_2$-TMZ even at a dose of 13.3 mg/kg has a long-acting increasing action on blood flow volume as compared with TMZ at a dose of 10 mg/kg. Although the venous return was not measured at the same time, said activity is presumed to be a peripheral blood vessel vasodilative action from the fact that the heart rate was not changed and from electrocardiographs of rabits.

(4) Influence on blood pressure at an opening of the coronary artery of a dog

| | | Highest blood pressure | Lowest blood pressure | Pulse |
|---|---|---|---|---|
| Compound of this invention, $n_2$-TMZ (n = 2) (dose: 20 mg/kg) | Control | 145.5 | 101.3 | 134 |
| | 2.5 mins, after administration | 137.6 | 83.1 | 128 |
| | 5 mins, after administration | 145 | 98.7 | 129 |
| (Comparison) SIN-1A (active metabolite of Molsidomine) (dose: 10 µg/kg) | Control | 135 | 92.2 | 138 |
| | 1 min, after administration | 137.6 | 85.7 | 165 |
| | 2.5 mins, after administration | | | 165 |

Judging from the preliminary experiment shown in the above table, it can be expected that for the compounds of this invention, there is a dose range in which they lower the lowest blood pressure without lowering the highest blood pressure and without changing the pulse.

What is claimed is:

1. A compound of the formula:

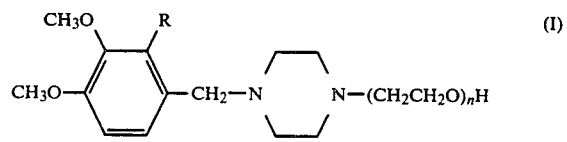

wherein R is hydrogen or a methoxy group; and n is an integer of 2 to 5, or a pharmaceutically acceptable acid addition salt thereof.

2. A compound according to claim 1, which is

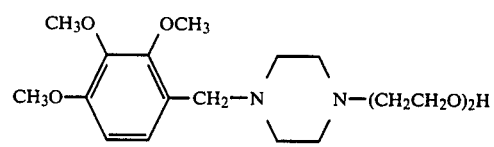

3. A compound according to claim 1, which is

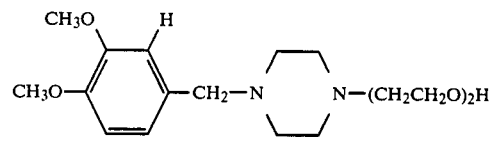

4. A pharmaceutical composition for improving blood circulation system comprising a therapeutically effective amount of a compound of the formula:

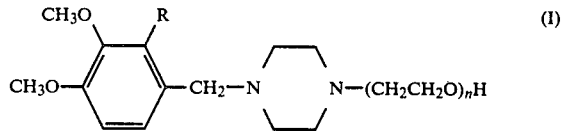

wherein R is hydrogen or a methoxy group; and n is an integer of 2 to 5, or a pharmaceutically acceptable acid addition salt thereof and a pharmaceutical carrier.

5. A composition according to claim 4, wherein the compound of the formula (I) is

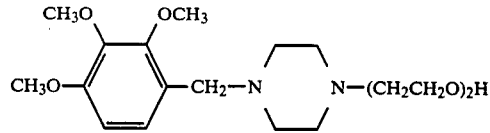

6. A composition according to claim 4, wherein the compound of the formula (I) is

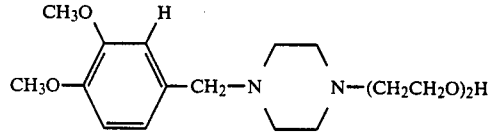

* * * * *